United States Patent [19]

Wuest et al.

[11] Patent Number: 4,659,701
[45] Date of Patent: Apr. 21, 1987

[54] VINYLBENZYL PHOSPHATES, AND THEIR USE FOR TREATING DERMALOGICAL DISORDERS

[75] Inventors: Hans-Heiner Wuest, Dossenheim; Fritz-Frieder Frickel, Deidesheim; Axel Nuerrenbach, Gruenstadt, all of Fed. Rep. of Germany

[73] Assignee: BASF Aktiengesellschaft, Fed. Rep. of Germany

[21] Appl. No.: 778,191

[22] Filed: Sep. 20, 1985

[30] Foreign Application Priority Data

Oct. 19, 1984 [DE] Fed. Rep. of Germany ....... 3438386

[51] Int. Cl.$^4$ .................. A61K 31/66; C07F 9/145
[52] U.S. Cl. .................................. 514/130; 514/143; 558/194; 558/197; 558/208
[58] Field of Search .............. 558/208, 194, 197; 514/130, 143

[56] References Cited

U.S. PATENT DOCUMENTS 4,326,055 4/1982 Loelinger ............... 260/410.9 R
4,578,498 3/1986 Frickel et al. ................. 514/532

*Primary Examiner*—Anton H. Sutto
*Attorney, Agent, or Firm*—Keil & Weinkauf

[57] ABSTRACT

A vinylbenzyl phosphate of the formula I

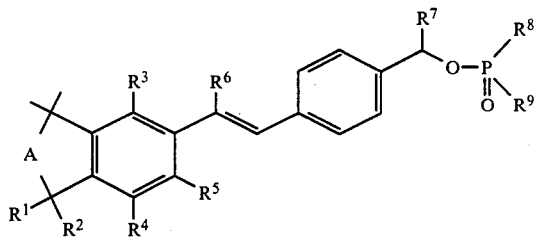

where A, $R^1$, $R^2$, $R^3$, $R^4$, $R^5$, $R^6$, $R^7$, $R^8$ and $R^9$ have the meanings stated in the description, and their preparation are described. The substances are useful for the treatment of disorders.

4 Claims, No Drawings

VINYLBENZYL PHOSPHATES, AND THEIR USE FOR TREATING DERMALOGICAL DISORDERS

The present invention relates to novel vinylbenzyl phosphates, processes for their preparation, and their use for the treatment of disorders.

It has been disclosed (German Laid-Open Applications DOS No. 2,854,354 and DOS No. 3,202,118) that stilbene derivatives have pharmacological effects in the topical and systemic therapy of neoplasias, acne, psoriasis and other dermatological affections.

We have found that vinylbenzyl phosphates of the formula I

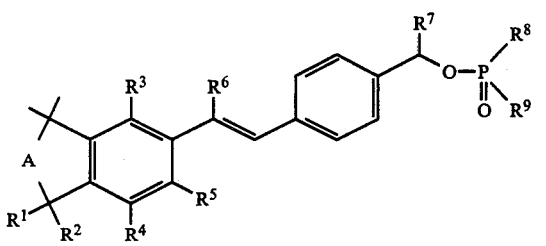

where A is a methylene or ethylene radical which is unsubstituted or substituted by $C_1$–$C_4$-alkyl, $R^1$ and $R^2$ are each hydrogen or methyl, $R^3$ is hydrogen, methyl, hydroxyl or $C_1$–$C_6$-alkoxy, $R^4$ and $R^5$ are each hydrogen, $C_1$–$C_4$-alkyl, methoxy or halogen, $R^6$ is hydrogen, $C_1$–$C_6$-alkyl or $C_3$–$C_6$-cycloalkyl, $R^7$ is hydrogen or $C_1$–$C_4$-alkyl and $R^8$ and $R^9$ are each a radical —$OR^{10}$ or —$NR^{11}R^{12}$, where $R^{10}$ is hydrogen, $C_1$–$C_8$-alkyl, aryl or aralkyl, $R^{11}$ and $R^{12}$ are each hydrogen or $C_1$–$C_6$-alkyl, or $R^{11}$ and $R^{12}$, together with the nitrogen atom to which they are bonded, form a heterocyclic radical, and two radicals $R^{10}$, $R^{11}$ and/or $R^{12}$ together in each case may furthermore be an ethylene or propylene group, and their physiologically tolerated salts possess a better action spectrum.

Preferred compounds are those wherein A is unsubstituted or methyl-substituted methylene or ethylene, $R^1$ and $R^2$ have the stated meanings, $R^3$, $R^4$ and $R^5$ are each hydrogen, $R^6$ is hydrogen or methyl and $R^9$ is hydroxyl or $C_1$–$C_4$-alkyl.

Where $R^{10}$ is aryl, it is preferably phenyl, while a preferred aralkyl group is benzyl which is unsubstituted or substituted on the phenyl group by methyl, methoxy or halogen. Preferred heterocyclic radicals —$NR^{11}R^{12}$ are pyrrolidino, piperidino and morpholino.

Typical examples of compounds according to the invention are:

4-[2-(5,6,7,8-Tetrahydro-5,5,8,8-tetramethylnaphth-2-yl)-1-propenyl]-benzyl phosphate 4-[2-(2,3-dihydro-1,1,3,3-tetramethyl-5-(1H)-indenyl)-1-propenyl]-benzyl phosphate 4-[2-(2,3-dihydro-1,1,2,3,3-pentamethyl-5-(1H)-indenyl)-1-propenyl]-benzyl phosphate 4-[2-(5,6,7,8-tetrahydro-3,5,5,8,8-pentamethylnaphth-2-yl)-1-propenyl-benzyl phosphate 4-[2-(5,6,7,8-tetrahydro-3-methoxy-5,5,8,8-tetramethyl naphth-2-yl)-1-propenyl]-benzyl phosphate 4-[2-(5,6,7,8-tetrahydro-1,3-dimethoxy-5,5,8,8-tetramethylnaphth-2-yl)-1-propenyl]-benzyl phosphate 4-[2-(5,6,7,8-tetrahydro-1,4-dimethoxy-5,5,8,8-tetramethylnaphth-2-yl)-1-propenyl]-benzyl phosphate 4-[2-(3-ethyl-5,6,7,8-tetrahydro-5,5,8,8-tetramethylnaphth-2-yl)-1-propenyl]-benzyl phosphate 4-[2-(5,6,7,8-tetrahydro-5,5,8,8-tetramethyl-3-(2-methylpropyl)naphth-2-yl)-1-propenyl]-benzyl phosphate 4-[2-(3-fluoro-5,6,7,8-tetrahydro-5,5,8,8-tetramethylnaphth-2-yl)-1-propenyl]-benzyl phosphate 4-[2-(5,6,7,8-tetrahydro-1-methoxy-3,5,5,8,8-pentamethylnaphth-2-yl)-1-propenyl]-benzyl phosphate 4-[2-(5,6,7,8-tetrahydro-1-methoxy-4,5,5,8,8-pentamethylnaphth-2-yl)-1-propenyl]-benzyl phosphate 4-[2-(5,6,7,8-tetrahydro-1-hydroxy-3,5,5,8,8-pentamethylnaphth-2-yl)-1-propenyl]-benzyl phosphate 4-[2-(1-hexoxy-5,6,7,8-tetrahydro-5,5,8,8-tetramethylnaphth-2-yl)-1-propenyl]-benzyl phosphate 4-[2-(1-ethoxy-5,6,7,8-tetrahydro-3,5,5,8,8-pentamethylnaphth-2-yl)-1-propenyl]-benzyl phosphate 4-[2-(5,6,7,8-tetrahydro-1,3,5,5,8,8-hexamethylnaphth-2-yl)-1-propenyl]-benzyl phosphate 4-[2-(5,6,7,8-tetrahydro-1,4,5,5,8,8-hexamethylnaphth-2-yl)-1-propenyl]-benzyl phosphate 4-[2-(5,6,7,8-tetrahydro-1,4-dimethoxy-3,5,5,8,8-hexamethyl)naphth-2-yl)-1-propenyl]-benzyl phosphate 4-[2-(5,6,7,8-tetrahydro-8,8-dimethylnaphth-2-yl)-1-propenyl]-benzyl phosphate 4-[2-(5,6,7,8-tetrahydro-3,8,8-trimethylnaphth-2-yl)-1-propenyl]-benzyl phosphate 4-[2-(5,6,7,8-tetrahydro-3,8,8-trimethylnaphth-2-yl)-1-ethenyl]-benzyl phosphate 4-[2-(5,6,7,8-tetrahydro-5,5,8,8-tetramethylnaphth-2-yl)-1-ethenyl]-benzyl phosphate 4-[2-(5,6,7,8-tetrahydro-3-methoxy-5,5,8,8-tetramethylnaphth-2-yl)1-ethenyl]-benzyl phosphate 4-[2-(5,6,7,8-tetrahydro-1,3-dimethoxy-5,5,8,8-tetramethylnaphth-2-yl)-1-ethenyl]-benzyl phosphate 4-[2-(5,6,7,8-tetrahydro-1,4-dimethoxy-5,5,8,8-tetramethylnaphth-2-yl)-1-ethenyl]-benzyl phosphate 4-[2-(5,6,7,8-tetrahydro-1-methoxy-3,5,5,8,8-pentamethylnaphth-2-yl)-1-ethenyl]-benzyl phosphate 4-[2-(5,6,7,8-tetrahydro-1-hydroxy-3,5,5,8,8-pentamethylnaphth-2-yl)-1-ethenyl]-benzyl phosphate 4-[2-(5,6,7,8-tetrahydro-5,5,8,8-tetramethylnaphth-2-yl)-1-buten(1)-yl]-benzyl phosphate 4-[2-(5,6,7,8-tetrahydro-5,5,8,8-tetramethylnaphth-2-yl)-octen(1)-yl]-benzyl phosphate 4-[2-(cyclopropyl-(5,6,7,8-tetrahydro-5,5,8,8-tetramethylnaphth-2-yl)-1-ethenyl]-benzyl phosphate 4-[3-(methyl-2-(5,6,7,8-tetrahydro-5,5,8,8-tetramethylnaphth-2-yl)-1-buten(1)-yl]-benzyl phosphate 4-[2-(5,6,7,8-tetrahydro-3,5,5,8,8-pentamethylnaphth-2-yl)-1-buten(1)-yl]-benzyl phosphate 4-[2-(2,3-dihydro-1,1,2,3,3,6-hexamethyl-5(1H)-indenyl)-ethyl]-benzyl phosphate 4-[2-(2,3-dihydro-1,1,3,3,6-pentamethyl-5(1H)-indenyl)-1-propenyl]-benzyl phosphate 4-[2-(2,3-dihydro-1,1,3,3,6-pentamethyl-5(1H)-indenyl)-1-ethenyl] ethenyl]-benzyl phosphate 4-[2-(2,3-dihydro-1,1,2,3,3,6-hexamethyl-5(1H)-indenyl)-1-propenyl]-benzyl phosphate 4-[2-(2,3-dihydro-1,1,2,3,3-pentamethyl-6-propyl-5(1H)-indenyl)-1-propenyl]-benzyl phosphate 4-[2-(2,3-dihydro-1,1,2,3,3-pentamethyl-5(1H)-indenyl)-1-ethenyl]-benzyl phosphate 1-[4-[2-(5,6,7,8-tetrahydro-5,5,8,8-tetramethylnaphth-2-yl)-1-propenyl]-phenyl]-propyl phosphate 1-[4-[2-(5,6,7,8-tetrahydro-5,5,8,8-tetramethylnaphth-2-yl)-1-propenyl]-phenyl]-pentyl phosphate 1-[4-[2-(5,6,7,8-tetrahydro-5,5,8,8-tetramethylnaphth-2-yl)-1-propenyl]-phenyl]-ethyl phosphate
2-methyl-1-[4-[2-(5,6,7,8-tetrahydro-5,5,8,8-tetramethylnaphth-2-yl)-1-propenyl]-phenyl]-ethyl phosphate
4-[2-(5,6,7,8-tetrahydro-5,5,8,8-tetramethylnaphth-2-yl)-1-propenyl]-benzyl dimethyl phosphate
4-[2-(5,6,7,8-tetrahydro-5,5,8,8-tetramethylnaphth-2-yl)-1-propenyl]-benzyl diethyl phosphate
4-[2-(5,6,7,8-tetrahydro-5,5,8,8-tetramethylnaphth-2-yl)-1-propenyl]-benzyl dibutyl phosphate
4-[2-(5,6,7,8-tetrahydro-5,5,8,8-tetramethylnaphth-2-yl)-1-propenyl]-benzyl dioctyl phosphate
4-[2-(5,6,7,8-tetrahydro-5,5,8,8-tetramethylnaphth-2-yl)-1-propenyl]-benzyl dibenzyl phosphate
4-[2-(5,6,7,8-tetrahydro-5,5,8,8-tetramethylnaphth-2-yl)-1-propenyl]-benzyl diphenyl phosphate
4-[2-(5,6,7,8-tetrahydro-5,5,8,8-tetramethylnaphth-2-yl)-1-propenyl]-benzyl methyl phosphate
4-[2-(5,6,7,8-tetrahydro-5,5,8,8-tetramethylnaphth-2-yl)-1-ethenyl]-benzyl diethyl phosphate
4-[2-(2,3-dihydro-1,1,2,3,3-pentamethyl-5(1H)-indenyl)-1-propenyl]-benzyl diethyl phosphate
phosphoric acid 4-[2-(5,6,7,8-tetrahydro-5,5,8,8-tetramethylnaphth-2-yl)-1-propenyl]-benzyl ester diamide
phosphoric acid 4-[2-(5,6,7,8-tetrahydro-5,5,8,8-tetramethylnaphth-2-yl)-1-propenyl]-benzyl ester bis(methylamide)
phosphoric acid 4-[2-(5,6,7,8-tetrahydro-5,5,8,8-tetramethylnaphth-2-yl)-1-propenyl]-benzyl ester bis(dimethylamide)
phosphoric acid 4-[2-(5,6,7,8-tetrahydro-5,5,8,8-tetramethylnaphth-2-yl)-1-propenyl]-benzyl ester bis(diethylamide)
phosphoric acid 4-[2-(5,6,7,8-tetrahydro-5,5,8,8-tetramethylnaphth-2-yl)-1-propenyl]-benzyl ester bis(benzylamide)
phosphoric acid 4-[2-(5,6,7,8-tetrahydro-5,5,8,8-tetramethylnaphth-2-yl)-1-propenyl]-benzyl ester bis-morpholide
2-[4-[2-(5,6,7,8-tetrahydro-5,5,8,8-tetramethylnaphth-2-yl)-1-propenyl]-benzyloxy]-1,3,2-dioxaphospholane 2-oxide
2-[4-[2-(5,6,7,8-tetrahydro-3,5,5,8-tetramethylnaphth-2-yl)-1-propenyl]-benzyloxy]-1,3,2-dioxophosphorinane 2-oxide
3-methyl-2-[4-[2-(5,6,7,8-tetrahydro-5,5,8,8-tetramethylnaphth-2-yl)-1-propenyl]-benzyloxy]-1,3,2-oxazaphospholane-2-oxide
3-methyl-2-[4-[2-(5,6,7,8-tetrahydro-5,5,8,8-tetramethylnaphth-2-yl)-1-propenyl]-benzyloxy]-1,3,2-oxaphosphorinane-2-oxide
1,3-dimethyl-2[4-[2-(5,6,7,8-tetrahydro-5,5,8,8-tetramethylnaphth-2-yl)-1-propenyl]-benzyloxy]-1,3,2-diazaphospholane-2-oxide.

The compounds of the formula I in which $R^8$ and/or $R^9$ are OH groups can form salts with 1 or 2 moles of a base. Examples of suitable salts are ammonium salts, alkali metal salts, in particular those of sodium, potassium and lithium, alkaline earth metal salts, in particular those of calcium and magnesium, and salts with suitable organic bases, such as lower alkylamines, e.g. methylamine or ethylamine, in particular cyclohexylamine, substituted lower alkylamines, in particular hydroxyl-substituted alkylamines, such as diethanolamine, triethanolamine or tris-(hydroxymethyl)-aminomethane, and piperidine and morpholine.

The novel vinylbenzyl phosphates can be prepared by a method in which (a) an alcohol of the formula II

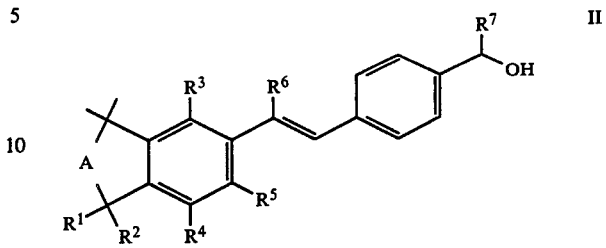

where A, $R^1$, $R^2$, $R^3$, $R^4$, $R^5$, $R^6$ and $R^7$ have the above meanings, is reacted with a phosphorylating reagent of the formula III

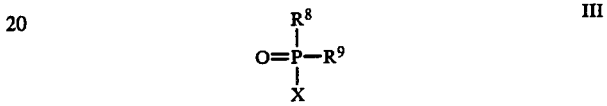

where $R^8$ and $R^9$ have the above meanings and X is halogen or an imidazole, N,N'-dicyclohexylisourea, trichloroacetimidate, p-toluenesulfonyloxy, p-nitrophenyloxy or mesityloxy radical or a group —O—P-(O)$R^8R^9$, or (b) an alcohol of the formula II is reacted, under oxidation conditions, with a phosphorylation reagent of the formula V

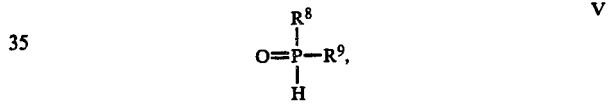

wherein $R^8$ and $R^9$ have the stated meanings, and, if desired, the resulting compound is converted to one of its physiologically tolerated salts.

Reaction (a) is usually carried out at from −20° to 100° C., depending on the type of phosphorylating reagent.

The acids formed during the reaction, for example hydrohalic acids, are advantageously bound using a base, particularly useful bases being tertiary nitrogen bases, such as pyridine, N,N-dimethylaniline, 2-picoline, 2,6-lutidine, imidazole or triethylamine, or hydrides or carbonates of the alkali metals, preferably those of sodium or of potassium. Acrylonitrile too can serve as an acid acceptor.

The reactions are usually carried out in the presence of a diluent, for example a hydrocarbon, such as benzene, toluene, xylene or petroleum ether, a polar aprotic solvent, such as acetone, butan-2-one, acetonitrile, dimethylformamide or dimethyl sulfoxide, or an ether, such as tetrahydrofuran, dioxane or dimethoxyethane. The above tertiary nitrogen bases too, when used in excess, can serve as solvents.

If one or both of the radicals $R^8$ and $R^9$ are hydroxyl, the trichloroacetimidate method is preferably used, X in formula (III) being the trichloroacetimidate radical. In this method, an alcohol of the formula (II) is reacted with anhydrous phosphoric acid or with a phosphate of the formula (III), where X is hydroxyl, and with trichloroacetonitrile in the presence of a base, e.g. triethylamine, at as high as 75° C., in the presence or absence of a solvent, such as acetonitrile, the trichloroacetimidates of the formula (III) being formed in situ.

Process (b) is preferably carried out in carbon tetrachloride and 50% strength sodium hydroxide solution under transfer-catalytic conditions. Particularly suitable catalysts are quaternary ammonium salts, such as tetrabutylammonium bromide.

The novel compounds of the formula (I), where $R^8$ and/or $R^9$ are hydroxyl, which are prepared by the stated processes, are advantageously first isolated as salts, preferably as mono- or bis-cyclohexylammonium phosphates, from which the free phosphoric mono- or diesters can be liberated by treatment with a dilute mineral acid or by means of an acidic ion exchanger.

The alcohols of the formula (II) which are used as starting compounds are obtained by reduction of the carboxylic acids or carboxylates of the formula (IV)

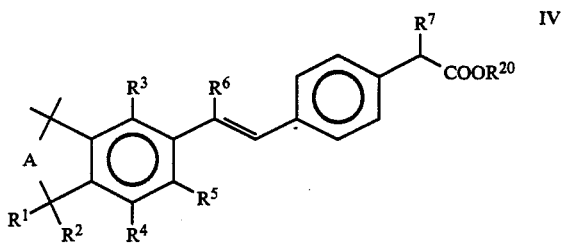

IV where A, $R^1$, $R^2$, $R^3$, $R^4$, $R^5$, $R^6$ and $R^7$ have the above meanings and $R^{20}$ is hydrogen or $C_1$-$C_4$-alkyl. Compounds of the formula (IV) are described in German Laid-Open Application DOS No. 2,894,354, or can be prepared by the methods described therein.

Because of their pharmacological properties, the novel compounds and their physiologically tolerated salts can be used in the topical and systemic therapy and prophylaxis of precanceroses and carcinomas of the skin, the mucous membranes and internal organs, in the topical and systemic therapy of acne, psoriasis and other dermatological disorders accompanied by pathologically changed cornification, and for the treatment of rheumatic disorders, in particular those of an inflammatory or degenerative nature which affect the joints, muscles, tendons and other parts of the locomotor system. Preferred areas of indication in addition to the therapy of dermatological disorders are the prophylactic and therapeutic treatment of precanceroses and tumors and the treatment of arthritic disorders. The dermatological activity, for example in the treatment of acne, can be demonstrated by, inter alia, determining the comedolytic activity and the ability to reduce the number of utriculi in the rhino mouse model. This method is described by L. H. Kligman et al. in The Journal of Investigative Dermatology 73 (1979), 354–358, and by J. A. Mezick et al. in Methods of Dermatology (Ed. Maibach, Lowe), vol. 2, pp. 59–63, Karger, Basel 1985. The antiarthritic action of the novel compounds can be determined in the conventional manner in animal experiments using the adjuvant arthritis model. The preventive action with regard to the formation and development of premalign lesions can be demonstrated, for example, in the test models below. In in vitro hamster tracheal tissue, the novel compounds eliminate the keratinization which sets in after vitamin A deficiency. This keratinization forms part of the early phase of carcinogenesis, which is inhibited in vivo by the novel compounds of the formula (I) using a similar technique after being induced by chemical compounds or high-energy radiation or after viral cell transformation. This method is described in Cancer Res. 36 (1976), 964–972, Nature 250 (1974), 64–66 and Nature 253 (1975), 47–50.

The compounds according to the invention also inhibit the proliferation rates of certain cells showing malignant changes. This method is described in J. Natl. Cancer Inst. 60 (1978), 1035–1041, Experimental Cell Research 117 (1978), 15–22 and Proc. Natl. Acad. Sci. USA 77 (1980), 2936–2940. Reference may also be made to the determination of the anatagonistic actions toward phorbol esters, which are described in Cancer Res. 37 (1977), 2196–2201.

Accordingly, the present invention furthermore relates to therapeutic agents for topical and systemic administration which contain a compound of the formula (I) as an active compound, in addition to conventional carriers or diluents, and to the use of a compound of the formula (I) for the preparation of a drug.

The therapeutic agents or formulations are prepared in a conventional manner, for example by mixing an appropriate dose of the active compound with conventional solid or liquid carriers or diluents and conventional pharmaceutical auxiliaries, in accordance with the desired route of administration.

Accordingly, the agents can be administered perorally, parenterally or topically. Examples of formulations of this type are tablets, film tablets, coated tablets, capsules, pills, powders, solutions or suspensions, infusion or injectable solutions, and pastes, ointments, gels, creams, lotions, dusting powders, solutions or emulsions and sprays.

The therapeutic agents can contain the compounds used according to the invention in a concentration of from 0.001 to 1%, preferably from 0.001 to 0.1%, for local administration, and preferably in a single dose of from 0.1 to 50 mg for systemic administration, and can be administered daily in one or more doses, depending on the nature and severity of the illness.

Examples of conventional pharmaceutical auxiliaries are alcohols, such as isopropanol, oxyethylated castor oil or oxyethylated hydrogenated castor oil, polyacrylic acid, glycerol monostearate, liquid paraffin, vaseline, wool fat, polyethylene glycol 400, polyethylene glycol 400 stearate and oxyethylated fatty alcohols for local administration, and lactose, propylene glycol, ethanol, starch, talc and polyvinylpyrrolidone for systemic administration. If required, an antioxidant, for example tocopherol, butylated hydroxyanisole or butylated hydroxytoluene, or flavor-improving additives, stabilizers, emulsifiers, lubricants, etc. may be added to the preparations. All substances used in the preparation of pharmaceutical formulations must be toxicologically acceptable and compatible with the active compounds used.

Preparation of the compounds according to the invention.

EXAMPLE 1

Monocyclohexylammonium salt of 4-[2-(5,6,7,8-tetrahydro-5,5,8,8-tetramethylnaphth-2-yl)-1-propenyl]-benzyl phosphate.

A solution of 6.06 g (0.06 mole) of anhydrous phosphoric acid, 12.2 g (0.12 mole) of triethylamine, 45.3 g of acetonitrile and 0.45 ml of water were added dropwise in the course of 55 minutes to 25.3 g (75.7 millimoles) of 4-[2-(5,6,7,8-tetrahydro-5,5,8,8-tetramethylnaphth-2-yl)-1-propenyl]-benzyl alcohol and 16.5 g (0.15 mole) of trichloroacetonitrile. The mixture was heated at 50° C. for a short time and stirred overnight at room temperature.

The mixture was poured onto 75 ml of water and extracted with ether until the ether phase no longer showed a yellow coloration (about 5×75 ml of ether), and the aqueous phase was evaporated down at a bath temperature of from 30° to 40° C. 6 g of cyclohexylamine and 60 ml of acetone were added, the mixture was left to stand overnight in a freezer, and the resulting crystals were filtered off and dried over phosphorus pentoxide in a drying oven under reduced pressure at 30° C. to give 16 g of crude product.

5 g of this crude product were substantially dissolved in 100 ml of a 1:1 mixture of chloroform and water, the solution was filtered from insoluble constituents, and the milky filtrate was left to stand for 2 days, the major part of the chloroform evaporating and a colorless crystalline precipitate being formed. This precipitate was filtered off and dried over phosphorus pentoxide to give 1.5 g of the title compound of melting point 235°–239° C.

EXAMPLE 2

Biscyclohexylammonium salt of 4-[2-(2,3-dihydro-1,1,2,3,3-pentamethyl-5(1H)-indenyl)-1-propenyl]-benzyl phosphate.

By a method similar to that in Example 1, 2.2 g of the title compound of melting point 206°–210° C. were obtained from 10 g (29 mmol) of 4-[2-(2,3-dihydro-1,1,2,3,3-pentamethyl-5(1H)-indenyl)-1-propenyl]-benzyl alcohol, 2.2 g (23 mmol) of phosphoric acid, 8.2 g (57 mmol) of trichloroacetonitrile and 4.5 g (45 mmol) of cyclohexyl amine.

EXAMPLE 3

4-[2-(5,6,7,8-tetrahydro-5,5,8,8-tetramethyl-2-naphthyl)-1-propenyl]-benzyl diethyl phosphate.

A solution of 3.5 g (25 mmol) of diethyl phosphite in 6 ml of carbon tetrachloride was added dropwise, while cooling with ice, to a mixture of 7 g (20 mmol) of 4-[2-(5,6,7,8-tetrahydro-5,5,8,8-tetramethyl-2-naphthyl)-1-propenyl]-benzyl alcohol, 12 ml of carbon tetrachloride, 0.16 g of tetrabutylammonium bromide and 6 ml of 50% strength sodium hydroxide solution. The mixture was stirred for 3 days at room temperature, then extracted with 30 ml of methylene chloride, the organic phase was washed with 10 ml of 2% strength hydrochloric acid and twice with 10 ml of water each time, and was dried over $Na_2SO_4$ and evaporated down. The residue was recrystallized from pentane and once again from petroleum ether, to give 0.3.g of the title compound of melting point 70°–74° C., which was 98% pure according to HPLC (C18 reverse phase; hexane/ethanol/0.1% strength acetic acid; 100 ml/min.).

We claim:

1. A vinylbenzyl phosphate of the formula I

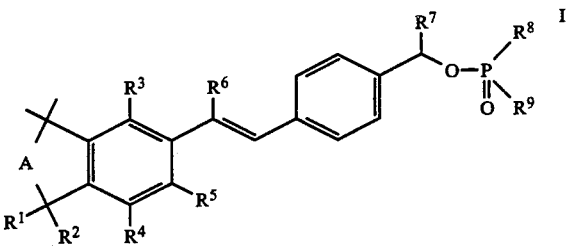

where A is a methylene or ethylene radical which is unsubstituted or substituted by $C_1$–$C_4$-alkyl, $R^1$ and $R^2$ are each hydrogen or methyl, $R^3$ is hydrogen, methyl, hydroxyl or $C_1$–$C_6$-alkoxy, $R^4$ and $R^5$ are each hydrogen, $C_1$–$C_4$-alkyl, methoxy or halogen, $R^6$ is hydrogen, $C_1$–$C_6$-alkyl or $C_3$–$C_6$-cycloalkyl, $R^7$ is hydrogen or $C_1$–$C_4$-alkyl and $R^8$ and $R^9$ are each a radical —$OR^{10}$ or —$NR^{11}R^{12}$, where $R^{10}$ is hydrogen, $C_1$–$C_8$-alkyl, aryl or aralkyl, $R^{11}$ and $R^{12}$ are each hydrogen or $C_1$–$C_6$-alkyl, and its physiologically tolerated salts.

2. The method of treating dermatological disorders in a patient suffering therefrom which comprises administering to the patient an effective amount of a compound as set forth in claim 1.

3. A vinylbenzyl phosphate of the formula I as set forth in claim 1, wherein A is unsubstituted or methyl-substituted methylene or ethylene, $R^1$ and $R^2$ have the stated meanings, $R^3$, $R^4$ and $R^5$ are hydrogen, $R^6$ is hydrogen or methyl and $R^9$ is hydroxyl or $C_1$–$C_4$-alkyl.

4. A therapeutic composition comprising a pharmaceutically acceptable carrier and an effective amount of a compound as set forth in claim 1 as the active compound. F

* * * * *

UNITED STATES PATENT AND TRADEMARK OFFICE
CERTIFICATE OF CORRECTION

PATENT NO. : 4,659,701

DATED : April 21, 1987

INVENTOR(S) : Hans-Heiner WUEST et al.

It is certified that error appears in the above-identified patent and that said Letters Patent is hereby corrected as shown below:

IN THE CLAIMS

Column 8, line 46, delete [F].

Signed and Sealed this

Eighth Day of September, 1987

Attest:

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,659,701
DATED     : April 21, 1987
INVENTOR(S) : Han-Heiner Wuest et al It is certified that error appears in the above-identified patent and that said Letters Patent is hereby corrected as shown below:

On the title page under Foreign Application Priority Data Insert

-- September 22, 1984 (DE) Fed. Rep. of Germany  3434945 --.

Signed and Sealed this

Sixteenth Day of February, 1988

Attest:

DONALD J. QUIGG

Attesting Officer

Commissioner of Patents and Trademarks